United States Patent [19]

Kroutil et al.

[11] Patent Number: 5,061,854
[45] Date of Patent: Oct. 29, 1991

[54] SHORT SCAN PASSIVE INFRARED REMOTE SENSOR

[75] Inventors: Robert T. Kroutil, Edgewood; John T. Ditillo, Baltimore; William R. Loerop, Aberdeen; Dennis M. Davis, Edgewood; Lynn D. Hoffland, Edgewood; Michael S. Desha, Baltimore, all of Md.

[73] Assignee: The United States of America as represented by the Secretary of the Army, Washington, D.C.

[21] Appl. No.: 513,536

[22] Filed: Apr. 10, 1990

[51] Int. Cl.$^5$ .............................. G01J 3/45
[52] U.S. Cl. .................. 250/339; 250/338.5
[58] Field of Search ............... 250/339, 338.5

[56] References Cited

U.S. PATENT DOCUMENTS

4,797,923  1/1989  Clarke ............................... 381/31
4,810,884  3/1989  Carlson ........................... 250/338.5

Primary Examiner—Constantine Hannaher
Attorney, Agent, or Firm—Anthony T. Lane; Edward Goldberg; Michael C. Sachs

[57] ABSTRACT

A short scan passive infrared remote sensor for detecting a target chemical species, located some distance from the center burst, includes a telescope for targeting a remote gas, a beam splitter means for splitting a beam from the target gas and sending one portion along a first path to an infrared detector and sending a second portion along a second path longer than the first path to the infrared detector. The second path is variable by providing a moving mirror a first distance away from the beam splitter which is 0.5 mm farther away from the beam splitter than the fixed mirror. By this arrangement, a mirror movement of only 0.5 mm is required to obtain an equivalent of 8 cm$^{-1}$ spectral information for processing with time domain digital filters. The information from the infrared detector is converted from analog to digital and fed to a digital signal processor. The resulting interferogram is then filtered by a microprocessor using a FIR linear digital filter.

4 Claims, 6 Drawing Sheets

SHORT SCAN PASSIVE INFRARED REMOTE SENSOR

GOVERNMENTAL INTEREST

The invention described herein may be made, use, or licensed by or for the Government for governmental purposes without the payment to us of any royalties thereon.

FIELD AND BACKGROUND OF THE INVENTION

Many toxic chemical compounds can be remotely detected by measuring the infrared spectrum between 8 and 12 microns. Typical instrumentation required to complete this measurement consists of a passive infrared sensor and a signal processor that operate in parallel to give an early warning of the toxic compound. The sensor detects the background radiation while the signal processor discriminates between toxic compounds, background signatures, and other non-toxic compounds.

SUMMARY AND OBJECTS OF THE INVENTION

It is an object of the invention to provide a short scan passive infrared remote sensor for the detection of a target chemical species which is located some distance from the sensor.

It is a further object of the invention to provide a short scan passive infrared remote sensor which may detect the chemical species of a target which sensor is small, compact and portable.

Still another object of the invention is to provide an infrared remote sensor as outlined above which can determine the chemical species using a small data processor while simultaneously providing the information in a relatively short amount of time.

To illustrate a method of detection of a target chemical species which is located at some distance from a sensor, one can consider the following theoretical description. If one totally fills the field-of-view (FOV) of a sensor, then the radiance incident on the sensor is the result of the radiances from:

1) the background (assumed to begin immediately behind the target cloud),
2) the target cloud and,
3) the intervening atmospheric gases.

The radiance from an infinitesimal layer is, $$N = \int_0^x \{k_T(\lambda)N_X(\lambda) - k_T(\lambda)N^1(\lambda) + k_A N_X(\lambda) - k_A N^1(\lambda)\}dx \quad (1)$$

where $k_T$ and $k_A$ are the extinction coefficients of the target gas and the atmosphere respectively with units of reciprocal length. $N_x$ is the radiance of the blackbody at the temperature of the infinitesimal layer. (The target gas is assumed to be at the temperature of the infinitesimal layer). $N^1$ is the radiance incident on the infinitesimal slab, traveling to the sensor, and x is a length variable which is independently integrated for range and target cloud length. All of these variables are functions of the wavelength as a function of the resolution of the instrument.

Assuming homogeneous atmospheric and target cloud species, integration of equation (1) gives the power incident on a passive sensor:

$$P = (T_A T_T N_{BG} + (1 - T_A T_T) N_T) A_c \Omega_s \quad (2)$$

where $T_A$ is the atmospheric transmittance, $T_T$ is the target cloud transmittance, $N_{BG}$ is the radiance of the background, $N_T$ is the radiance of a blackbody at the ambient temperature, $A_c$ is the collector area, $\Omega_s$ is the solid angle of acceptance of the sensor. The atmospheric cloud transmittance is:

$$T_A = e^{-k_A R} \quad (3)$$

where R is the distance to the target cloud. The target cloud transmittance, is $$T_T = e^{-k_T L} = e^{-\alpha_T C l} \quad (4)$$

where $\alpha_T$ (m²/mg) is the absorptivity of the target cloud, C is the concentration of the target cloud (mg/m₃) and L is the length of the target cloud (m). It is assumed that $R >> L$.

Two factors are implicit in equation 2. The first is that under normal conditions, $N_{BG}$ and $N_T$ differ at most by a few percent. If $N_T = N_{BG}$, then $P = N_{BG} A_c \Omega_s$ and the incoming radiation contains no information about the spectral properties of gases in the intervening atmosphere, although the magnitude of P remains about the same. Therefore, if detection is to occur, it is essential, that $N_{BG} - N_T = \Delta N > 0$. The temperature associated with a given radiance level and optical wavelength can be determined from Plank's function. Therefore, the required difference can be interpreted in terms of the temperature. There is an occasional question as to whether the necessary difference should be interpreted in terms of air temperatures or equivalent radiometric temperatures of the target cloud and the background. The interpretation to some degree depends on the constraints of the model. In this case, the target cloud is assumed to be sufficiently small with the temperature being the primary criteria. That is, the air temperature of the target cloud and the effective radiometric temperature of the background, regardless of the emissivity of the cloud, is a primary consideration. The temperature of the background is more difficult to define under conditions of good atmospheric transmittance. The measured radiometric temperature results from integration over a long path, which is nonhomogeneous with respect to temperature, species and concentration. The effective temperature generally varies with wavelength of the radiation. When atmospheric transmittance becomes low, the range becomes short and the background temperature approaches the local temperature and becomes more easily identified with a particular air mass. This lack of precise knowledge of temperature does not cause particularly difficult detection problems, but it places severe limits on the measurement capabilities of passive systems. The second factor implicit in equation (2) is the signal due to the target not being 1/R² dependent as long as the target cloud fills the field-of-view. The signal does depend on atmospheric transmittance which is range dependent.

The problem requires that an extremely small temperature difference be measured from a remote distance. Of all techniques used only the Michelson interferometer has the sensitivity and optical bandwidth necessary for detection. The sensitivity is based on two advantages which are the optical throughput (Jacquinot's advantage) and the multiplex advantage (Fellgett's advantage).

Despite its advantage, the standard Michelson interferometer has several serious limitations for passive remote sensing. The first limitation is that to process the data in real time for a collection rate of 30 scans per second, requires serious demands on the computer processor. Currently, this either requires a large computer or a very expensive array processor. The second limitation is that the interferometer and its associated electronics are generally required to have a linear response over a 16 fold range. This severe limitation requires the use of a gain ranged analog-to-digital converter in order to record the time domain data. The third limitation is the vibration sensitivity question. In the collection of interferogram, data errors can arise because of the inexact positioning of the moving mirror of a Michelson interferometer.

Accordingly, it is an object of the invention to provide an arrangement for passive remote sensing which solves the problems as detailed above.

According to the invention, a modified short scan interferometer is provided for detecting specific toxic gases. The arrangement includes a beam splitter, a stationary mirror, an infrared detector and a moving mirror. An 8 bit analog-to-digital converter is provided coupled to a digital signal processing chip which is adapted to perform signal processing on time domain data. According to the invention, the moving mirror is preferably positioned at 0.5 mm distance farther away from the beam splitter than the fixed mirror. By this arrangement, mirror movement of only 0.5 mm is required to obtain an equivalent 8 cm$^{-1}$ spectral information for processing with time domain digital filters. This is significantly superior to a conventional Michelson interferometer using a standard Fourier transform, requiring a mirror movement of 0.5 cm to obtain an equivalent 8 cm$^{-1}$ spectral resolution. Because time domain data is not collected near to the center burst, the dynamic range of the short scan interferometer according to the invention, is reduced. Accordingly, equivalent dynamic range information can be obtained using the inventive short scan interferometer to dynamic range information obtained from conventional Michelson interferometers, even when using an 8 bit analog-to-digital converter.

Although the central burst contains information from all spectral wave lengths, the central burst contains a disproportionate amount of information concerned with the background radiation. Separation of these spectral features can be performed by apodizing, clipping, or deconvolving the central burst of the interferogram.

Among the appropriate apodizing or clipping functions, are finite-impulse response filters wherein the filter is of the form:

$$Y = f_1 Y_{i-n} + \ldots + f_{n+1} Y_i$$

where:
Y is a filtered data point;
$Y_i$ is a data point corresponding to Y;
$f_1, \ldots, f_i, \ldots, f_n, f_{n+1}$ are waiting coefficients.
Other forms of digital filters include matrix filters and infinite-impulse filters.

(1) It is an object of the invention to reduce scanning mechanism distances and improve tolerances required for mirror drive mechanisms and to collect the equivalent of an 8 wavenumber infrared spectrum. The mirror is placed approximately 0.5+X mm from the center burst, where X is the equivalent distance from the mirror. All spectral information needed for a toxic gas detector can be obtained by moving the mirror a distance of only 0.5 mm.

(2) The 16 bit Analog-to-Digital converter used with a gain ranging can be reduced to a digitizing board that contains only an 8 bit analog converter with no gain ranging. The net result is a significant reduction in the electronic hardware required.

(3) The short scan interferogram can be processed by a simple digital filter. The digital filter processing of a short scan reduces digital processing requirements by at least a factor of three. By using digital signal processor (DSP) hardware, a factor of 100 fold improvement in processing time over the Fourier transformation should be obtained.

(4) A mathematical digital filter can be used to process data from this short scan interferometer and discriminate the signatures between the background and those that contain toxic gaseous compounds.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

In order to eliminate these three basic limitations of the Michelson interferometer, a detailed analysis was completed of the signals present in an interferogram collected with a passive infrared sensor. The analysis indicated that a "window" existed in which the simulant features were present but the background spectral features were not present.

Figure 1:
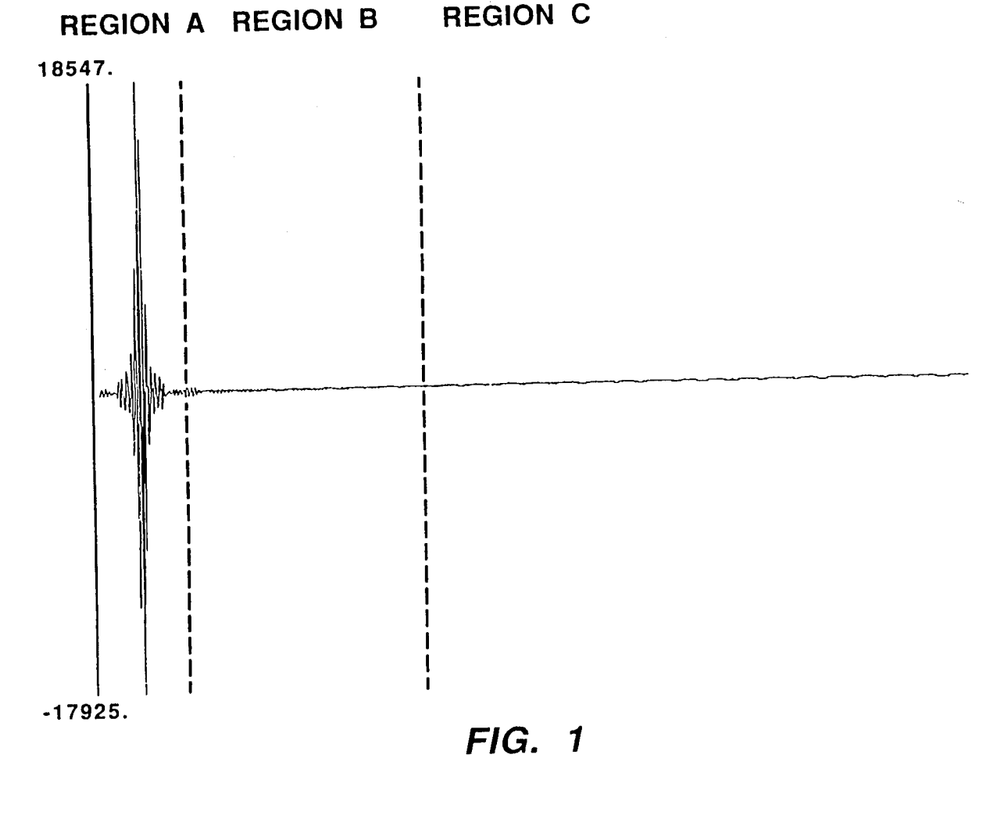
FIG. 1 is an interferogram, collected from a passive remote chemical sensor, broken into three distinguishable regions.

FIG. 1 shows an interferogram collected from a U.S. Army XM21 passive remote chemical sensor. According to the invention, for analysis, the interferogram may be divided into three sections. The first section contains the center burst of the interferogram. The center burst occurs when the distance is the same in both arms of a standard Michelson interferometer. When the mirror distance is the same, all of the wavelengths are additive in nature and constructive interference does not occur. Background spectral features are concentrated in this section along with signatures that exist from the simulants. As one moves away from the center burst region, the contribution from the background is exponentially reduced. This effect gives a region that contains spectrometer noise plus simulant spectral features. The third section of the interferogram contains very high resolution information. It can be shown that the points from 600 to 1024 in a 1024 point interferogram contain a very high component of spectrometer noise.

The present invention provides a modified short scan interferometer which makes use of these three regions in a passive infrared interferometer which can be used as a specific toxic gas detector.

Figure 2:
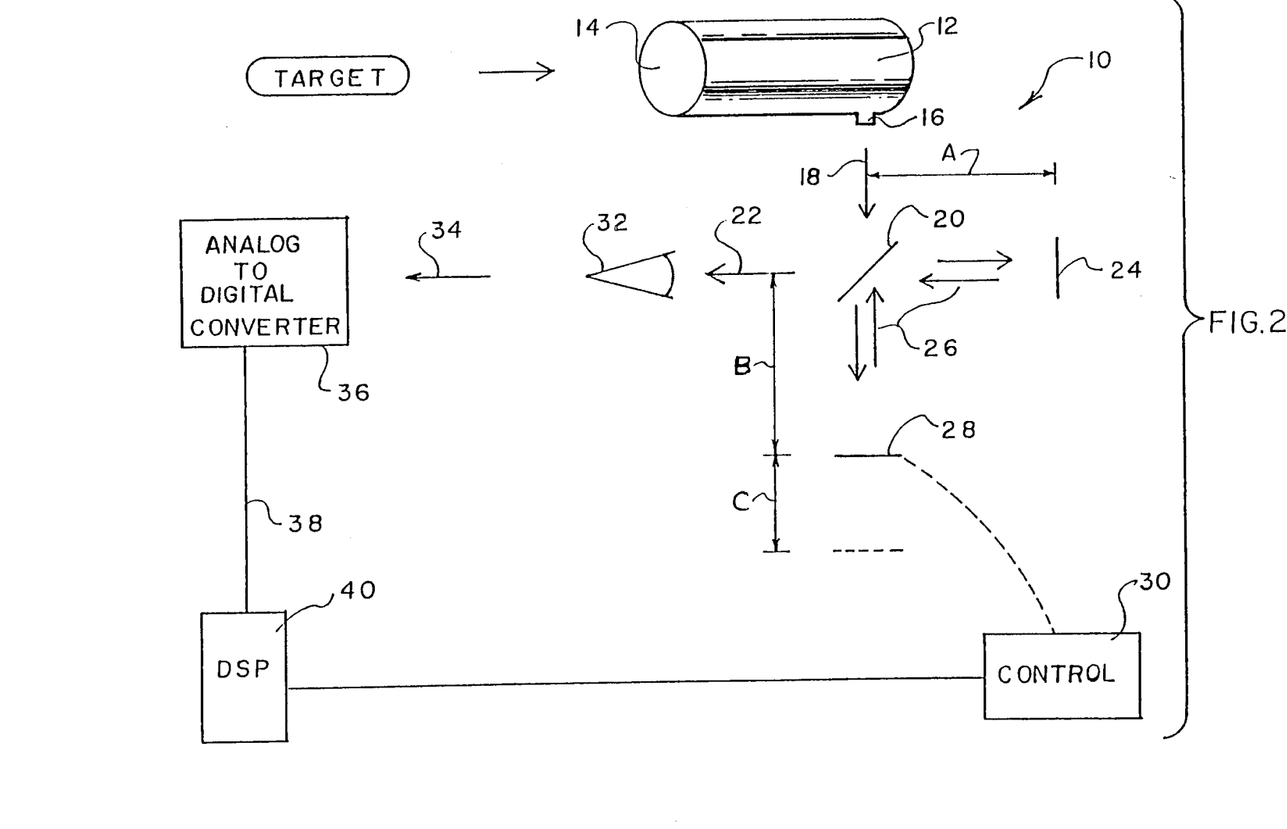
FIG. 2 is a diagrammatic view of a short scan passive infrared spectrometer in accordance with the invention.

Referring to FIG. 2 in particular, the invention embodied therein comprises a short scan passive infrared spectrometer generally designated 10. The spectrometer arrangement includes a telescope such as a 3:1 cassegrain telescope 12 which receives infrared energy at an input end 14 and outputs an adjusted proportional signal at output 16. The adjusted proportional signal 18 is fed to a beam splitting arrangement 20 which splits the signal into a first portion 22 which is directed directly to a detector 32 and other portions, generally designated as 26, which are directed to a movable mirror 28 and to a fixed mirror 24.

Fixed mirror 24 is positioned a fixed distance A from the beam splitter as seen in FIG. 2.

Moving mirror 28 is positioned between a distance B from the beam splitter to a distance C spaced from the distance B (see FIG. 2). The minimum distance B has been determined to be is 0.5 mm plus the distance A. That is, it has been determined that the scanning mechanism distance may be improved resulting in improved tolerance requirements for the mirror drive mechanisms by collecting the equivalent of an 8 wavenumber infrared spectrum by placing the mirror 28 approximately 0.5 plus X mm from the center burst, where X is the equivalent distance from mirror A. Accordingly, distance B equals 0.5 mm +distance A. The movement range C of the mirror 28 then is within a range of only 0.5 mm. This range is enough to obtain all spectral information of a toxic gas. The moving mirror 28 is connected to a moving mirror drive 30 for movement within the range C. Based on the position of the moving mirror 28 signals reflected from fixed mirror 24 and moving mirror 28 are directed to an infrared 32 detector which senses the signal impinging on the detector 32 and outputs an analog signal representative of the spectral information detected by the infrared detector 32. This analog signal 34 is directed to the analog-to-digital converter 36. As discussed above, the analog-to-digital converter is one with no gain ranging, thereby further reducing the complexity and size of the electronic hardware required.

Interferogram segments collected from a short scan interferometer 10 may be analyzed using several available Digital Signal Processor hardware components 40. Several commercially available integrated digital circuits have the capability of allowing designers to build algorithm specific digital signal processing circuits around host processors such as Intel 8026, Motorola 68000.

According to the preferred embodiment, the collected signal 38 from the 8 bit analog-to-digital converter 36 electronics is provided to a Harvard-architecture DSP microprocessor 40. The interferogram is then filtered by the microprocessor 40 using a FIR linear digital filter.

The precision of the infrared vapor chemical simulant spectral features was checked with regard to detection over a short section located 0.5 mm away from the center burst. A U.S. Army XM21 infrared spectrometer with a 0.5 cm mirror travel path length was positioned on a tripod mount with a 450 degree Kelvin hot blackbody source and a 0.98 cubic meter gas cell that contained the chemical simulant Sulfur Hexafloride ($SF_6$). The hot blackbody source was used to collect an XM21 interferogram that was "clipped". A "clipped" interferogram is one time domain scan of a moving mirror that overflows the dynamic range of the 16 bit analog-to-digital converter of the sensor. Several thousand interferograms were collected that contained the hot blackbody source and also the hot source plus the Sulfur Hexafloride simulant. Because the data was "clipped" the resulting data collected between points 150 and 350 of the 1024 point XM21 interferogram contained data that was of at least 8 bit resolution. The final step of this experiment was to mathematically zero all of the XM21 data points collected outside of the interferogram "window" from point 150 to point 350. The final step simulates the action of a short scan mechanism because only data collected in the short scan region 0.5 mm away from the center burst was used for further calculations.

Figure 3A:
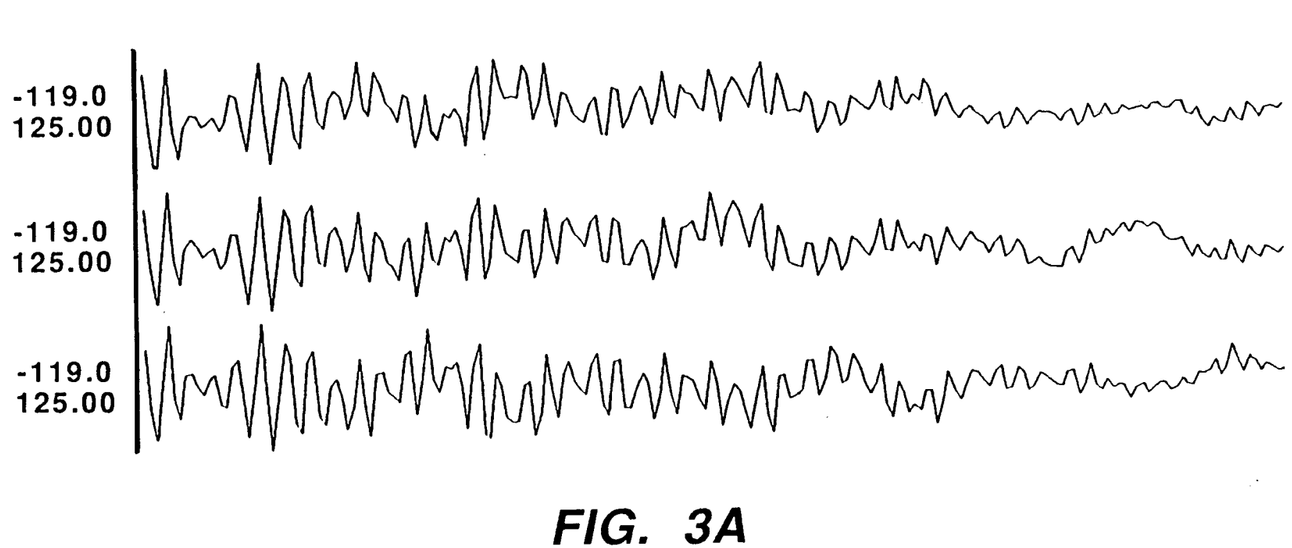
FIG. 3a is a short scan interferogram with a simulant present.
Figure 3B:
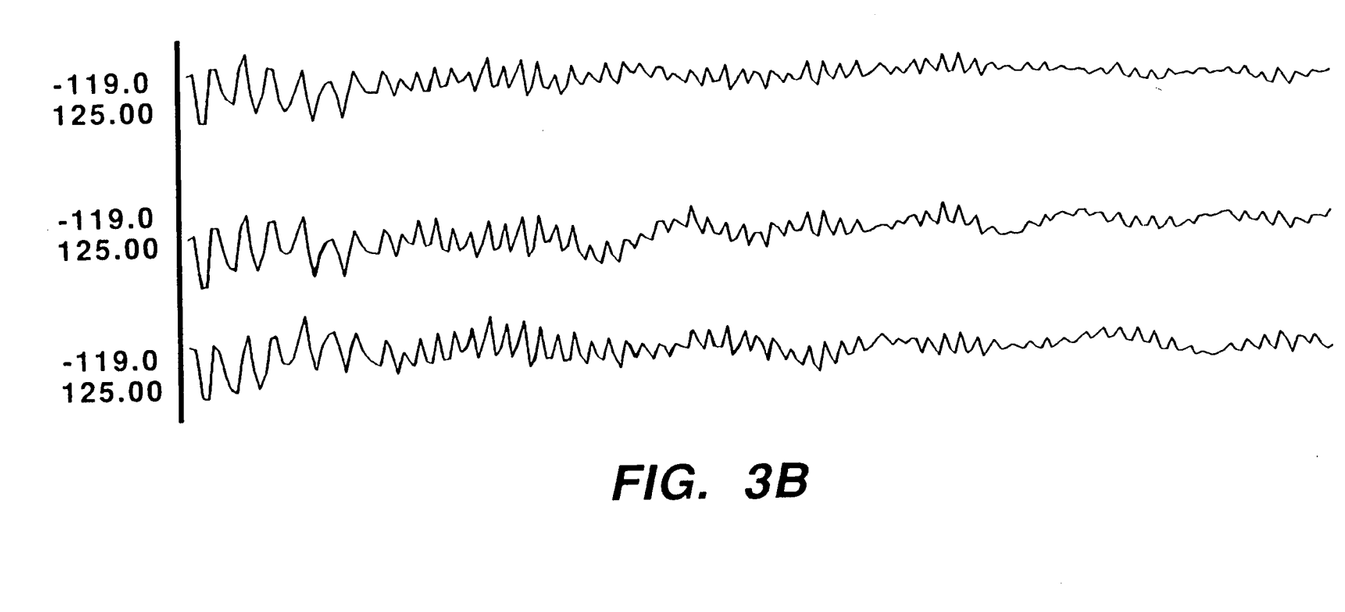
FIG. 3b is a short scan interferogram with no simulant present.
Figure 4A:
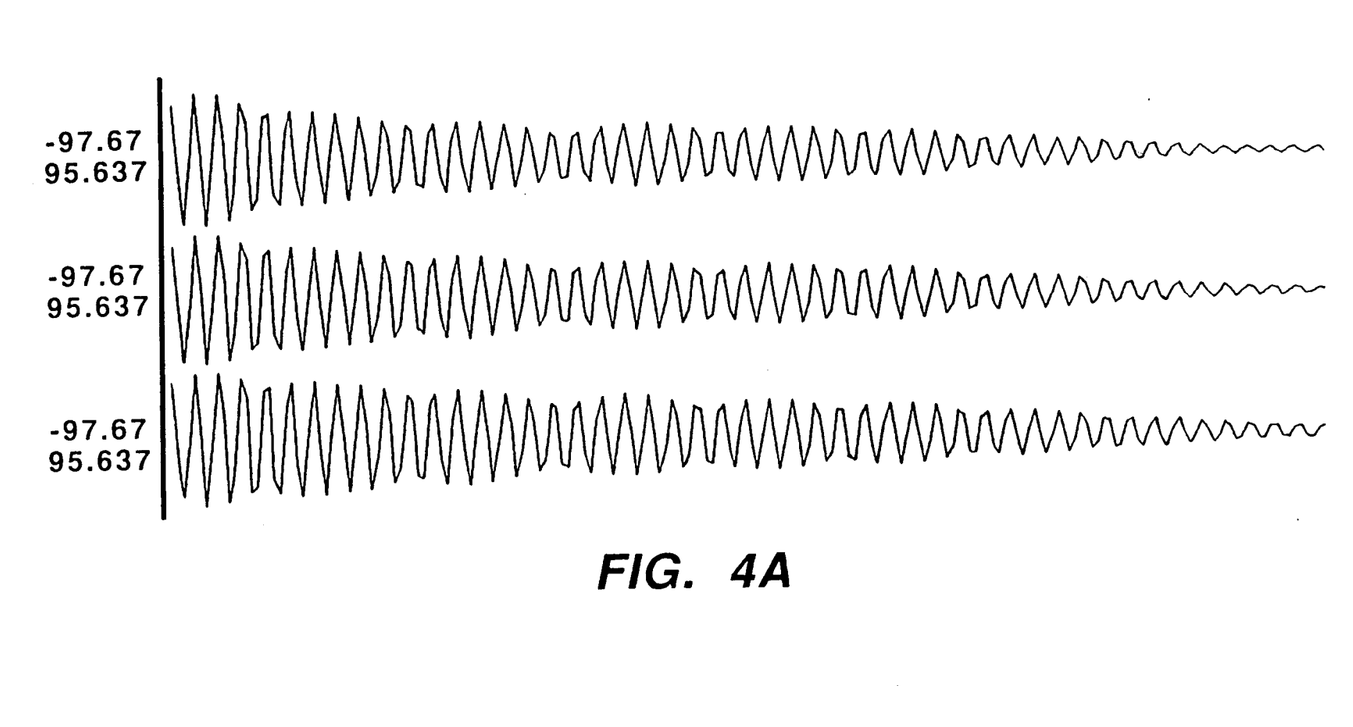
FIG. 4a is a filtered short scan interferogram with a simulant present.
Figure 4B:
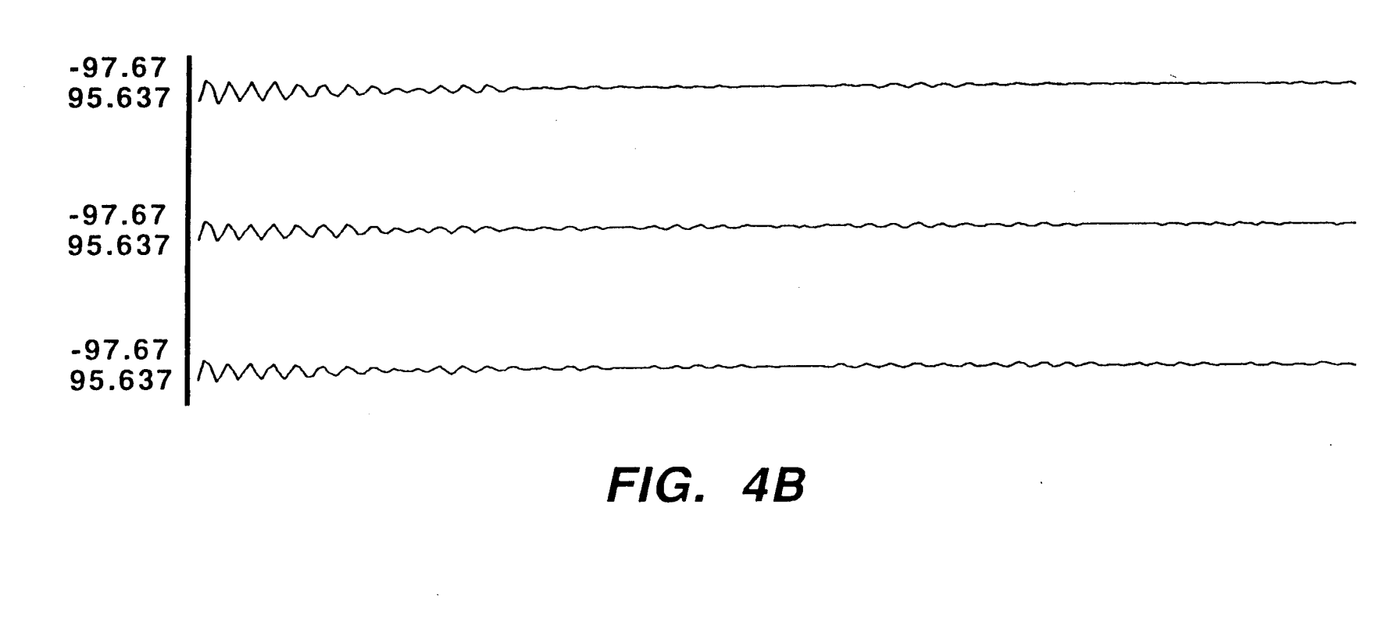
FIG. 4b is a filtered short scan interferogram with no simulant present.

Six raw experimental short scan interferograms collected from the experimental apparatus are shown in FIGS. 3A and 3B for a mirror travel distance of 0.5 mm. In FIG. 3B, the three interferograms contain background emission spectral signatures while, in FIG. 3A, the three interferograms contain background plus simulant spectral features. FIGS. 4B and 4A, respectively, show the same six interferograms after use of a time domain digital filter that was tuned specifically to the frequency of absorption of the Sulfur Hexalfloride simulant. The digital filter is used to eliminate background spectral features that contribute to the interferogram between points 150 and 350. In FIG. 4A it is apparent that a fundamental frequency exists in the three interferograms (simulant plus background) while, in FIG. 4B, almost no signal remains for the three interferograms (background only). It should be noted that the experimental processing scheme used was an offline computer simulation of capabilities which exist with current Harvard-architecture DSP microprocessors.

The reduction in computer processing is readily apparent from the results shown in Table 1. The computation times are shown for 32 1024 point interferograms using an optimized 512 Fourier transform and an unoptimized 20 term linear digital filter. Both computations were made on a Honeywell DPS 6/45 minicomputer with 1 megabyte of memory. It should be noted that the optimized Fourier transform was written in Honeywell DPS 6 Assembler code while the un-optimized 20 term linear digital filter was written in Fortran 77. Significant savings for the linear digital filter can be obtained by using an 8 term linear digital filter and converting the subroutine to Honeywell DPS 6 Assembler.

TABLE I

| COMPUTATION TIMES | |
|---|---|
| Process type | Processing time in seconds for 32 1024 point interferograms |
| Fourier transformation (Honeywell DPS 6/45 - optimized) | 63 seconds |
| 20 term linear digital filter (Honeywell DPS | 20 seconds |

TABLE I-continued

COMPUTATION TIMES

| Process type | Processing time in seconds for 32 1024 point interferograms |
|---|---|
| 6/45 - optimized) (Honeywell Fortran-77) | |

The experimental results shown in FIGS. 3A, 3B, 4A, and 4B indicate that an interferometer which scans only a small region (point 150 to point 300 of a 1204 point 8 wavenumber interferogram) can be used to identify toxic chemical clouds. In summary, it is claimed that the short scan interferometer described in the above paragraphs has the aforementioned advantages.

While a specific embodiment of the invention has been shown and described in detail to illustrate the application of the principles of the invention, it will be understood that the invention may be embodied otherwise without departing from such principles.

What is claimed is:

1. A short scan, passive infrared, toxic detector device for remotely detecting the presence of toxic gaseous compounds within a scanned atmospheric area, said device comprising an optical means for sensing infrared energy present in said scanned atmospheric area and producing an optical beam proportional to such sensed infrared energy, said detector device further comprising a means for isolating a select wave number band of energy within said optical beam, said means for isolating comprising:

beam splitting means for receiving said optical beam and splitting said optical beam into a first portion and a second portion, said beam splitting means directing said first portion in a first direction and directing said second portion in a second direction;

fixed mirror means spaced a fixed distance from said beam splitting means in said first direction;

moving mirror means spaced a minimum distance from said beam splitter equal to said fixed distance plus 0.5 mm and moveable within a range from a minimum distance of 0.5 mm, said moving mirror means for receiving said second portion;

analog outputting means for receiving reflected said first and second portions and for outputting an analog signal representative of an 8 wavenumber infrared spectrum;

analog-to-digital converter means for receiving said analog signal and for producing a corresponding digital signal; and, digital microprocessor means for receiving said digital signal and for discriminating select gas signatures amongst the background signatures and various other toxic gaseous compound signatures, wherein said digital signal microprocessor includes a FIR linear digital filter for filtering said digital signal, said filter being of the form, $Y = f_1 Y_{i-n} + \ldots + f_{n+1} Y_i$ where Y is a filtered data point, $Y_i$ is a data point corresponding to Y, and $f_1, \ldots f_i, \ldots, f_n, f_{n+1}$ are waiting coefficients.

2. A sensor according to claim 1, wherein said moving mirror means is connected to moving means for moving said mirror within said 0.5 mm range.

3. A sensor according to claim 2, wherein said moving means includes a servo device connected to a servo control, said servo control being connected to said digital signal microprocessor for adjustment of said moving mirror by said digital signal microprocessor.

4. A remote sensor according to claim 1, wherein said optical means includes a 3:1 cassegrain telescope having an input end directable at a target cloud.

* * * * *